(12) United States Patent
Huang et al.

(10) Patent No.: US 11,304,892 B2
(45) Date of Patent: Apr. 19, 2022

(54) ALTEROMONAS MACLEODII DOW02-2 AND ITS METABOLITES FOR IMPROVING SKIN MOISTURIZATION

(71) Applicant: TCI Co., Ltd., Taipei (TW)

(72) Inventors: Chu-Han Huang, Taipei (TW); Huan-You Lin, Taipei (TW); Cheng-Yu Ho, Taipei (TW); Yung-Hsiang Lin, Taipei (TW)

(73) Assignee: TCI Co., Ltd., Taipei (TW)

( * ) Notice: Subject to any disclaimer, the term of this patent is extended or adjusted under 35 U.S.C. 154(b) by 210 days.

(21) Appl. No.: 16/720,949

(22) Filed: Dec. 19, 2019

(65) Prior Publication Data

US 2020/0237647 A1    Jul. 30, 2020

Related U.S. Application Data

(60) Provisional application No. 62/783,379, filed on Dec. 21, 2018.

(51) Int. Cl.

| | |
|---|---|
| *C12N 1/20* | (2006.01) |
| *A61K 8/99* | (2017.01) |
| *A61K 35/74* | (2015.01) |
| *A61Q 19/00* | (2006.01) |
| *A61K 8/36* | (2006.01) |
| *A23L 33/135* | (2016.01) |

(52) U.S. Cl.
CPC ............. *A61K 8/99* (2013.01); *A23L 33/135* (2016.08); *A61K 8/36* (2013.01); *A61K 35/74* (2013.01); *A61Q 19/007* (2013.01); *C12N 1/20* (2013.01)

(58) Field of Classification Search
CPC . A61K 8/99; A61K 8/36; A61K 8/365; C12N 1/20; C12N 5/0829
See application file for complete search history.

(56) References Cited

PUBLICATIONS

Eckert, Richard L., et al., "Transglutaminase Function in Epidermis," *J Invest Dermatol*, vol. 124, No. 3, pp. 481-492 (2005).
Kumar, Vinod, et al., "A keratin scaffold regulates epidermal barrier formation, mitochondrial lipid composition, and activity," *J. Cell Biol.*, vol. 211, No. 5, pp. 1057-1075 (2015).
Sandilands, Aileen, et al., "Filaggrin in the frontline: role in skin barrier function and disease," *Journal of Cell Science*, vol. 122, No. 9, pp. 1285-1294 (2009).
Sayo, Tetsuya, et al., "Hyaluronan Synthase 3 Regulates Hyaluronan Synthesis in Cultured Human Keratinocytes," *The Journal of Investigative Dermatology*, vol. 118, pp. 43-48 (2002).

*Primary Examiner* — Tekchand Saidha
(74) *Attorney, Agent, or Firm* — Christensen, Fonder, Dardi & Herbert PLLC (57) ABSTRACT

*Alteromonas macleodii* Dow02-2 is provided, wherein the *Alteromonas macleodii* Dow02-2 was deposited at German Collection of Microorganisms and Cell Cultures (Deutsche Sammlung von Mikroorganismen and Zellkulturen, DSMZ) under the accession number DSM33380, and its metabolites comprise 2-hydroxy-3-methylbutyric acid. A method for providing 2-hydroxy-3-methylbutyric acid is also provided, wherein the method comprises isolating the 2-hydroxy-3-methylbutyric acid from metabolites of *Alteromonas macleodii* Dow02-2 of biologically pure culture. A method for at least one of increasing expression of TGM1 gene, increasing expression of KRT1 gene, increasing expression of KRT10 gene, increasing expression of KRT14 gene, increasing expression of FLG gene, increasing expression of GBA gene, and increasing expression of HAS3 gene is also provided, wherein the method comprises administering to a subject in need thereof an effective amount of 2-hydroxy-3-methylbutyric acid.

6 Claims, 10 Drawing Sheets

Specification includes a Sequence Listing.

SEQUENCE LISTING

```
<160> NUMBER OF SEQ ID NOS: 1

<210> SEQ ID NO 1
<211> LENGTH: 1320
<212> TYPE: DNA
<213> ORGANISM: Alteromonas macleodii
<220> FEATURE:
<223> OTHER INFORMATION: 16S rRNA fragment

<400> SEQUENCE: 1
ccagagtttg atcatggctc agattgaacg ctggcggcag gcctaacaca tgcaagtcga      60
acggtaacat ttctagcttg ctagaagatg acgagtggcg gacgggtgag taatgcttgg     120
gaacttgcct ttgcgagggg gataacagtt ggaaacgact gctaataccg cataatgtct     180
tcggaccaaa cggggcttag gctccggcgc aaagagaggc ccaagtgaga ttagctagtt     240
ggtaaggtaa cggcttacca aggcgacgat ctctagctgt tctgagagga agatcagcca     300
cactgggact gagacacggc ccagactcct acgggaggca gcagtgggga atattgcaca     360
atggggggaa ccctgatgca gccatgccgc gtgtgtgaag aaggccttcg ggttgtaaag     420
cactttcagt tgtgaggaaa agttagtagt taatacctgc tagccgtgac gttaacaaca     480
```

-continued

```
gaagaagcac cggctaactc cgtgccagca gccgcggtaa tacggagggt gcgagcgtta    540
atcggaatta ctgggcgtaa agcgcacgca ggcggtttgt taagctagat gtgaaagccc    600
cgggctcaac ctgggatggt catttagaac tggcagacta gagtcttgga gaggggagtg    660
gaattccagg tgtagcggtg aaatgcgtag atatctggag gaacatcagt ggcgaaggcg    720
actccctggc caaagactga cgctcatgtg cgaaagtgtg ggtagcgaac aggattagat    780
accctggtag tccacaccgt aaacgctgtc tactagctgt gtgtgccttt aaggcgtgcg    840
tagcgaagct aacgcgctaa gtagaccgcc tggggagtac ggccgcaagg ttaaaactca    900
aatgaattga cggggcccg cacaagcggt ggagcatgtg gtttaattcg atgcaacgcg     960 aagaaccta cctacacttg acatgctgag aagttactag agatagtttc gtgccttcgg    1020
gaactcagac acaggtgctg catggctgtc gtcagctcgt gtcgtgagat gttgggttaa   1080
gtcccgcaac gagcgcaacc cttgtcctta gttgccagcc ttaagttggg cactctaagg   1140
agactgccgg tgacaaaccg gaggaaggtg gggacgacgt caagtcatca tggcccttac   1200
gtgtagggct acacacgtgc tacaatggca tttacagagg gaagcgagac agtgatgtgg   1260
agcggacccc ttaaagaatg tcgtagtccg gattggagtc tgcaactcga ctccatgaag   1320
```

ALTEROMONAS MACLEODII DOW02-2 AND ITS METABOLITES FOR IMPROVING SKIN MOISTURIZATION

PRIORITY CLAIM

The present application claims priority to U.S. Provisional Patent Application No. 62/783,379, filed on Dec. 21, 2018, which said application is incorporated by reference in its entirety herein.

FIELD OF THE INVENTION

The present invention relates to the uses of a novel *Alteromonas macleodii* Dow02-2 (deposited at German Collection of Microorganisms and Cell Cultures (Deutsche Sammlung von Mikroorganismen and Zellkulturen, DSMZ) under the accession number DSM33380) and its metabolite(s), wherein the metabolite(s) of *Alteromonas macleodii* Dow02-2 comprises 2-hydroxy-3-methylbutyric acid, and 2-hydroxy-3-methylbutyric acid is effective in increasing expression of TGM1 gene, increasing expression of KRT1 gene, increasing expression of KRT10 gene, increasing expression of KRT14 gene, increasing expression of FLG gene, increasing expression of GBA gene, and increasing expression of HAS3 gene, and thus, can be used for improving skin moisturization.

BACKGROUND OF THE INVENTION

Skin is the largest protective barrier of human body. Since keratinocytes are arranged neatly, skin could effectively protect the body from moisture loss, pathogen invasion and various environmental damages. However, if the moisture content of skin is decreased, keratinocytes will not perform their metabolism normally and will accumulate on the surface of skin, and thus, may cause the skin to look dry and rough and cause symptoms such as dermatitis and acne. The aforesaid symptoms not only lead to the change of appearance, but also make the protective ability of the skin barrier weak. Therefore, if skin moisturization can be improved, problems such as skin dryness, skin roughness, dermatitis and acne will be mitigated.

It is known that many ingredients (e.g., hyaluronic acid, collagen, ceramide, urea, squalene, glycerol, N-acetylglucosamine (NAG) and vitamin B5) and natural extracts (e.g., aloe gel, seaweed gel, jojoba oil, shea butter) are effective in moisturizing skin. Because of the appearance consideration and health needs, people have paid more attention to skincare and devoted particular care to the use of natural and safe materials for skin caring. Therefore, the industry continuously develops effective means of skincare by using natural and safe materials.

Inventors of the present invention selected an *Alteromonas macleodii* Dow02-2 from deep ocean water, and found that 2-hydroxy-3-methylbutyric acid comprised in the metabolites of the strain is effective in increasing expression of TGM1 gene, increasing expression of KRT1 gene, increasing expression of KRT10 gene, increasing expression of KRT14 gene, increasing expression of FLG gene, increasing expression of GBA gene, and increasing expression of HAS3 gene, and thus, can be used for improving skin moisturization.

SUMMARY OF THE INVENTION

An objective of the present invention is to provide an *Alteromonas macleodii* Dow02-2, which was deposited at German Collection of Microorganisms and Cell Cultures (Deutsche Sammlung von Mikroorganismen und Zellkulturen, DSMZ) under the accession number DSM33380, wherein the *Alteromonas macleodii* Dow02-2 is provided by a biologically pure culture.

Another objective of the present invention is to provide a composition, comprising metabolites of the *Alteromonas macleodii* Dow02-2, wherein the metabolites of *Alteromonas macleodii* Dow02-2 comprise 2-hydroxy-3-methylbutyric acid. Preferably, the composition is a pharmaceutical composition, a food composition or a cosmetic composition. Preferably, the composition essentially consists of the metabolites of *Alteromonas macleodii* Dow02-2. More preferably, the composition consists of (i) the metabolites of *Alteromonas macleodii* Dow02-2, and (ii) a carrier, an additive and/or a vehicle.

Still another objective of the present invention is to provide a use of the *Alteromonas macleodii* Dow02-2 in providing 2-hydroxy-3-methylbutyric acid, wherein the 2-hydroxy-3-methylbutyric acid is isolated from the metabolites of *Alteromonas macleodii* Dow02-2.

Yet another objective of the present invention is to provide a use of 2-hydroxy-3-methylbutyric acid in the manufacture of a composition, wherein the composition is used for at least one of increasing expression of TGM1 gene, increasing expression of KRT1 gene, increasing expression of KRT10 gene, increasing expression of KRT14 gene, increasing expression of FLG gene, increasing expression of GBA gene, and increasing expression of HAS3 gene. Preferably, the 2-hydroxy-3-methylbutyric acid is provided in a form of the metabolites of *Alteromonas macleodii* Dow02-2, and the composition is a pharmaceutical composition, a food composition or a cosmetic composition.

Yet another objective of the present invention is to provide a use of 2-hydroxy-3-methylbutyric acid in improving skin moisturization. Preferably, the 2-hydroxy-3-methylbutyric acid is provided in a form of the metabolites of *Alteromonas macleodii* Dow02-2, and the metabolites or 2-hydroxy-3-methylbutyric acid is used in a form of a food composition or a cosmetic composition.

Yet another objective of the present invention is to provide a method for providing 2-hydroxy-3-methylbutyric acid, wherein the method comprises isolating the 2-hydroxy-3-methylbutyric acid from the metabolites of *Alteromonas macleodii* Dow02-2.

Yet another objective of the present invention is to provide a method for at least one of increasing expression of TGM1 gene, increasing expression of KRT1 gene, increasing expression of KRT10 gene, increasing expression of KRT14 gene, increasing expression of FLG gene, increasing expression of GBA gene, and increasing expression of HAS3 gene, wherein the method comprises administering to a subject in need an effective amount of 2-hydroxy-3-methylbutyric acid. Preferably, the 2-hydroxy-3-methylbutyric acid is administered to the subject in a form of a pharmaceutical composition, a food composition or a cosmetic composition. Preferably, the 2-hydroxy-3-methylbutyric acid is used in a form of the metabolites of *Alteromonas macleodii* Dow02-2.

Yet another objective of the present invention is to provide a method for improving skin moisturization, wherein the method comprises administering to a subject in need an effective amount of 2-hydroxy-3-methylbutyric acid. Preferably, the 2-hydroxy-3-methylbutyric acid is administered to the subject in a form of a food composition or a cosmetic composition. Preferably, the 2-hydroxy-3-methylbutyric acid is used in a form of the metabolites of *Alteromonas macleodii* Dow02-2.

The detailed technology and preferred embodiments implemented for the present invention are described in the following paragraphs for persons skilled in the art to well appreciate the features of the claimed invention.

DESCRIPTION OF THE PREFERRED EMBODIMENT

The following paragraphs will describe some of the embodiments of the present invention in detail. However, without departing from the spirit of the present invention, the present invention may be embodied in various embodiments and should not be limited to the embodiments described in the specification or defined in the appended claims.

Unless otherwise indicated herein, the expression "a," "an," "the," or the like recited in the specification of the present invention (especially in the claims) are intended to include both the singular and plural forms; the term "metabolite(s)" recited herein is not limited to a bacterial solution (i.e., a medium containing bacteria) obtained by culturing bacteria and may also refer to a product (e.g. a supernatant, a fraction or a concentrated solution) obtained by subjecting the aforesaid bacterial solution to a solid-liquid separation (e.g., centrifugation, filtration) or a separation/purification (e.g. column chromatography, vacuum concentration); the term "biologically pure culture" recited herein refers to that the desired bacterium is cultured in a culture environment in the absence of other microorganisms (i.e., undesired bacteria); the term "subject" recited herein refers to human or non-human mammalian (e.g., dog, cat).

The numerical ranges (e.g., 5 to 100) recited in this specification should be construed as including all of the rational numbers in the ranges and the ranges consisting of any rational numbers in the ranges. Therefore, the numerical ranges recited in this specification should include all the possible combinations of numerical values between the lowest value and the highest value listed therein. In addition, the word "about" presenting before the values as used herein substantially represents the values that can be increased or decreased in a normal and reasonable amount that a person having ordinary skill in the art considers acceptable. For example, the word "about" presenting before the values as used herein substantially represents values within ±10% of the stated value and more preferably within ±5%.

It was revealed by research that the expression levels of genes such as transglutaminase 1 (TGM1), keratin (KRT; such as KRT1, KRT10 and KRT14), filaggrin (FLG), β-glucocerebrosidase (GBA) and hyaluronan synthase 3 (HAS3) are associated with skin moistrurization, wherein transglutaminase 1 is an essential enzyme for forming a cornified envelope with a water-proof effect, keratin is one of primary components for constituting skin, filaggrin can be decomposed into natural moisturizing factor (NMF) by enzymes, β-glucocerebrosidase is an enzyme associated with ceramide synthesis in cells, and hyaluronan synthase 3 is an enzyme associated with hyaluronic acid synthesis in cells. The above facts can be noted in "Transglutaminase Function in Epidermis. *J Invest Dermatol.* 124(3):481-492 (2005)," "A keratin scaffold regulates epidermal barrier formation, mitochondrial lipid composition, and activity. *J. Cell Biol.* 211(5):1057-1075 (2015)," "Filaggrin in the frontline: role in skin barrier function and disease. Journal of Cell Science. 122(9):1285-1294 (2009)," and "Hyaluronan Synthase 3 Regulates Hyaluronan Synthesis in Cultured Human Keratinocytes. *The Journal of Investigative Dermatology* 118: 43-48 (2002)," which are entirely incorporated hereinto by reference. Therefore, if the expression levels of the aforementioned genes can be increased, the effect of improving skin moisturization will be achieved.

Inventors of the present invention selected an *Alteromonas macleodii* Dow02-2 from deep ocean water, analyzed the strain by 16S rRNA gene sequence analysis, and identified the strain as an *Alteromonas macleodii* based on the phylogenetic relationship, and thus, named the strain as *Alteromonas macleodii* Dow02-2, which has been deposited at German Collection of Microorganisms and Cell Cultures (Deutsche Sammlung von Mikroorganismen and Zellkulturen, DSMZ) under the accession number DSM33380. The *Alteromonas macleodii* Dow02-2 has a 16S rRNA fragment as shown in SEQ ID NO: 1.

Inventors of the present invention found that the metabolites of *Alteromonas macleodii* Dow02-2 comprise 2-hydroxy-3-methylbutyric acid, and both the metabolites and 2-hydroxy-3-methylbutyric acid are effective in increasing expression of TGM1 gene, increasing expression of KRT1 gene, increasing expression of KRT10 gene, increasing expression of KRT14 gene, increasing expression of FLG gene, increasing expression of GBA gene, and increasing expression of HAS3 gene, and, thus can be used for improving skin moisturization.

Therefore, the present invention relates to a strain selected from the deep ocean (i.e., *Alteromonas macleodii* Dow02-2) and uses of its metabolites, and the aforesaid uses include: a composition comprising the metabolites of *Alteromonas macleodii* Dow02-2; a use of *Alteromonas macleodii* Dow02-2 in providing 2-hydroxy-3-methylbutyric acid; a use of 2-hydroxy-3-methylbutyric acid in the manufacture of a composition for increasing expressions of TGM1 gene, KRT1 gene, KRT10 gene, KRT14 gene, FLG gene, GBA gene and/or HAS3 gene; a use of 2-hydroxy-3-methylbutyric acid in improving skin moisturization; a method for providing 2-hydroxy-3-methylbutyric acid; a method for increasing expressions of at least one of TGM1 gene, KRT1 gene, KRT10 gene, KRT14 gene, FLG gene, GBA gene and HAS3 gene, comprising administering to a subject in need an effective amount of 2-hydroxy-3-methylbutyric acid; and a method for improving skin moisturization, comprising administering to a subject in need an effective amount of 2-hydroxy-3-methylbutyric acid. In the aforesaid uses, the 2-hydroxy-3-methylbutyric acid can be provided, used or administered to the subject in a form of the metabolites of *Alteromonas macleodii* Dow02-2.

The metabolites of *Alteromonas macleodii* Dow02-2 adopted in accordance with the present invention could be generated by culturing *Alteromonas macleodii* Dow02-2 under an environment suitable for its growth. For example, *Alteromonas macleodii* Dow02-2 can be firstly cultured with a suitable medium, and then, the solids such as bacteria in the medium thus obtained can be optionally removed to obtain an *Alteromonas macleodii* Dow02-2's metabolites-containing liquid.

To provide the desired metabolites, any suitable medium can be chosen and used to perform the culture of *Alteromonas macleodii* Dow02-2, as long as the medium can provide the desired nutrients (e.g., yeast extract, protein and glucose) and conditions (e.g., pH value, sodium content) for the growth and metabolism of *Alteromonas macleodii* Dow02-2. Furthermore, the time period for culturing *Alteromonas macleodii* Dow02-2 is not specifically limited, as long as the time period is sufficient for the *Alteromonas macleodii* Dow02-2 to complete at least one metabolic cycle. For example, in one embodiment of the present invention, *Alteromonas macleodii* Dow02-2 was cultured with a seawater-like medium for 18 hours to let the strain metabolize and generate metabolites.

In the use of *Alteromonas macleodii* Dow02-2 in providing 2-hydroxy-3-methylbutyric acid in accordance of the present invention, a medium that has undergone the metabolic cycles of *Alteromonas macleodii* Dow02-2 can be directly used, wherein the medium contains the *Alteromonas macleodii* Dow02-2 and its metabolites. Otherwise, an *Alteromonas macleodii* Dow02-2's metabolites-containing liquid, from which the solids such as *Alteromonas macleodii* Dow02-2 have been removed, can be used. Any suitable procedure can be employed to remove the solids, as long as the procedure does not adversely affect the desired effects of the metabolites (comprising 2-hydroxy-3-methylbutyric acid) generated after culturing the *Alteromonas macleodii* Dow02-2. Generally, physical approaches, such as centrifugal separation, filter filtration, precipitation and decantation, can be employed to remove the solids. Optionally, the above procedures can be repeated or combined to remove solids (including bacteria) from the medium as much as possible.

Besides isolating and purifying from the metabolites of *Alteromonas macleodii* Dow02-2 to provide 2-hydroxy-3-methylbutyric acid, the 2-hydroxy-3-methylbutyric acid adopted in accordance with the present invention can also be provided by any suitable methods. For example, the 2-hydroxy-3-methylbutyric acid can be provided by using chemical synthesis or by isolating/purifying from materials comprising 2-hydroxy-3-methylbutyric acid.

The pharmaceutical composition provided in accordance with the present invention can be administered to a subject in need systemically or topically, and can be delivered by various drug delivery systems (DDSs), such as an oral drug delivery system, transdermal drug delivery system, injectable drug delivery system, etc. For example, to enhance bioavailability, control drug release speed, target the lesion precisely and reduce side effects, the pharmaceutical composition can be delivered by a liposome, a microcapsule, nanoparticles, or microneedles, but is not limited thereby.

Depending on the desired purpose(s), the pharmaceutical composition of the present invention can be provided in any suitable form without particular limitations. For example, the pharmaceutical composition can be provided in a form for oral administration, intravenous injection (including drip infusion and bolus injection), intramuscular injection, subcutaneous injection, intraarterial injection, intraperitoneal injection or transdermal (such as patch, ointment, etc.) administration, but is not limited thereby. Depending on the form and purpose(s), a suitable carrier can be chosen and used to provide the pharmaceutical composition, wherein the carriers are well known by a person skill in the art of pharmaceutical engineering. Examples of the carrier include excipients, diluents, auxiliaries, stabilizers, absorption enhancers, disintegrating agent, hydrotropic agents, emulsifiers, antioxidants, adhesives, binders, tackifiers, dispersants, suspending agents, lubricants, hygroscopic agents, etc.

As a form for oral administration, the pharmaceutical composition can be provided by any suitable methods in any suitable form for oral administration, wherein the suitable liquid form for oral administration includes syrups, an oral solution, a suspension, an elixir, etc., and the suitable solid form for oral administration includes a powder, a granule, a troche, a dragee, an enteric-coated tablet, a chewable tablet, an effervescent tablet, a film coated tablet, a capsule, a long-acting slow-release tablet, etc. The pharmaceutical composition provided in accordance with the present invention can comprise any pharmaceutically acceptable carrier that will not adversely affect the desired effects of the active ingredient (i.e., 2-hydroxy-3-methylbutyric acid). For example, the pharmaceutically acceptable carriers of the aforesaid liquid form include, but are not limited to, water, saline, dextrose, glycerol, ethanol or its analogs, oil (e.g., olive oil, castor oil, cottonseed oil, peanut oil, corn oil, and germ oil), glycerol, polyethylene glycol, and combinations thereof and the pharmaceutically acceptable carriers of the aforesaid solid form include, but are not limited to, cellulose, starch, kaolinite, bentonite, sodium citrate, gelatin, agar, carboxymethyl cellulose, gum arabic, seaweed gel, glyceryl monostearate, calcium stearate, and combinations thereof.

As a form for transdermal administration, the pharmaceutical composition of the present invention can also comprise any pharmaceutically acceptable carrier that will not adversely affect the desired effects of the active ingredient (i.e., 2-hydroxy-3-methylbutyric acid), such as water, mineral oil, propylene glycol, polyethylene oxide, liquid petrolatum, sorbitan monosterate, and polysorbate 60. The pharmaceutical composition can be provided by any suitable methods in any suitable form for transdermal administration, such as in the form of an emulsion, a cream, an oil, a gel (such as a hydrogel), a paste (such as a dispersing paste, an ointment), a lotion, a spray, a patch (such as a microneedle patch), etc., but is not limited thereby.

As for the form of injections or drips, the pharmaceutical composition can comprise one or more ingredient(s), such as an isotonic solution, a salt-buffered saline (e.g., phosphate-buffered saline or citrate-buffered saline), a hydrotropic agent, an emulsifier, a 5% sugar solution, and other carriers to provide the pharmaceutical composition as an intravenous infusion, an emulsified intravenous infusion, a powder for injection, a suspension for injection, or a powder suspension for injection, etc. Alternatively, the pharmaceutical composition could be prepared as a pre-injection solid. The desired injection is provided by dissolving the pre-injection solid in other solutions or suspensions or emulsifying it prior to being administered to a subject in need.

The food composition provided in accordance with the present invention can be a beverage, a solid food or a semi-solid food, and can be provided in a form of a health food, a daily supplement, a functional food, a nutritional supplement or a special nutritional food. For example, the food composition can be manufactured as dairy products, meat products, breads, pasta, cookies, frozen desserts, troche, capsule, fruit juices, teas, sparkling water, alcoholic drinks, sport drinks, nutritional drinks, ablactational food, etc., but is not limited thereby. Preferably, the food composition is provided in a form of a health food or a daily supplement.

In addition, depending on the form and needs, the food composition in accordance with the present invention can comprise any suitable food additives. For example, the food additives include, but is not limited to, a preservative, a bactericide, an antioxidant, a bleaching agent, a color fasting agent, a swelling agent, a nutrition additive, a colorant, a flavoring agent (e.g., sweetener), a pasting agent, a binding agent, chemicals for food industry, an emulsifier, and agents for improving quality, brewing and food processing.

The recommended daily dosage, use standards and use conditions for a specific population (e.g., pregnant woman, kids, etc.), or the recommendations for a use in combination with another food product or medicament can be indicated on the exterior package of the health food, daily supplement, functional food, nutritional supplement, and/or special nutritional food provided in accordance with the present invention. Thus, it is suitable for the user to take the health food, daily supplement, functional food, nutritional supplement, and/or special nutritional food by him- or herself safely and securely without the instructions of a doctor, pharmacist, or related executive.

The cosmetic composition provided in accordance with the present invention can be produced in any suitable product forms. For example, the cosmetic composition can be a care product such as softening lotion, convergent lotion, nutritional lotion, nutritional cream, massage cream, essence, eye cream, eye essence, facial mask, patch, spray, body lotion, body cream, body oil, and body essence, etc.; a makeup product such as makeup primer, foundation, face powder, blush, eyeshadow, brow powder, mascara, lipstick, etc.; or a cleaning product such as cleaning oil, cleaning cream, cleaning lotion, eye and lip makeup remover, soap, body wash, etc. In addition, the cosmetic composition can also be used in a foam form or an aerosol form further containing a compressed propellant.

Depending on the form and needs of product, the cosmetic composition provided in accordance with the present invention can comprise any cosmetically or dermatologically acceptable vehicles that will not adversely affect the desired effects of the active ingredient (i.e., 2-hydroxy-3-methylbutyric acid). For example, when the cosmetic composition is an emulsion, cream or gel product, ingredients such as wax, paraffin, starch, tragacanth gum, cellulose derivatives, animal oil, plant oil, mineral oil, polyethylene glycol, bentonite, silicon oxide, talc, zinc oxide can be used as the vehicle; when the cosmetic composition is a powder or aerosol product, ingredients such as lactose, talc, silicon oxide, aluminum hydroxide, calcium silicate, polyamide can be used as the vehicle; when the cosmetic composition is a solution or emulsion product, ingredients such as water, ethanol, isopropanol, ethyl carbonate, ethyl acetate, benzyl alcohol, benzyl benzoate, propylene glycol, polyethylene glycol can be used as the vehicle, but is not limited thereby.

When the cosmetic composition is provided in the form of a cleaning product, the cosmetic composition can further comprise any surfactants that will not adversely affect the desired effects of the active ingredients (i.e., 2-hydroxy-3-methylbutyric acid) as the vehicle, wherein examples of the surfactants include, but are not limited to, fatty acid salts, alkylbenzene sulfonate (ABS), fatty alcohol sulfate (FAS), alcohol ether sulfate (AES), fatty alcohol polyoxyethylene ether carboxylate (AEC), fatty acid methyl ester sulfonate (MES), fatty alcohol ethoxylates (AE), alkyl polyglycoside (APG), betaine type surfactant, and combinations thereof.

Optionally, the pharmaceutical composition or cosmetic composition provided in accordance with the present invention can also comprise a suitable amount of additives, such as a toner or a colorant for enhancing the visual perception of the pharmaceutical composition or cosmetic composition, and/or a buffer, a conservative, a preservative, an antibacterial agent, or an antifungal agent for improving the stability and storability of the pharmaceutical composition or cosmetic composition.

The pharmaceutical, food or cosmetic composition provided in accordance with the present invention can optionally further comprise one or more other active ingredient(s) (e.g. hyaluronic acid, collagen, ceramide, urea, squalene, glycerol, N-acetylglucosamine (NAG), vitamin B5, aloe gel, seaweed gel, jojoba oil, shea butter) to further enhance the effects of the pharmaceutical, food or cosmetic composition, or to increase the application flexibility and application adaptability of preparation thus provided, as long as the other active ingredients do not adversely affect the desired effects of the active ingredient of the present invention (i.e., 2-hydroxy-3-methylbutyric acid).

The pharmaceutical, food or cosmetic composition provided in accordance with the present invention contains at least about 0.0001, 0.0002, 0.0003, 0.0004, 0.0005, 0.001, 0.0015, 0.002, 0.0025, 0.003, 0.0035, 0.004, 0.0045, 0.005, 0.0055, 0.006, 0.0065, 0.007, 0.0075, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 5, 10, 15, 20, 25, 30, 35, 40, 45, 50, 55, 60, 65, 70, 75, 80, 85, 90, 95 or 100 wt % of the active ingredient (i.e., 2-hydroxy-3-methylbutyric acid)

based on the total weight of the composition, and useful ranges may be selected from any two of these values, for example from about 0.0001 wt % to about 90 wt %, about 0.001 wt % to about 25 wt %, about 0.01 wt % to about 10 wt %, about 0.01 wt % to about 5 wt %, about 0.05 wt % to about 1 wt % and about 0.05 wt % to about 0.5 wt %.

Depending on the need, age, body weight and health conditions of the subject and the purpose of application, the pharmaceutical, food or cosmetic composition provided in accordance with the present invention can be taken at various frequencies, such as once a day, multiple times a day, or once every few days, etc. The amount of 2-hydroxy-3-methylbutyric acid in the pharmaceutical, food or cosmetic composition provided in accordance with the present invention can be adjusted, for example, to the amount that it should be taken or external used daily, depending on the need in the practical application.

As described above, the present invention also provides a method for at least one of increasing expression of TGM1 gene, increasing expression of KRT1 gene, increasing expression of KRT10 gene, increasing expression of KRT14 gene, increasing expression of FLG gene, increasing expression of GBA gene, increasing expression of HAS3 gene, and improving skin moisturization, comprising administering to a subject in need an effective amount of 2-hydroxy-3-methylbutyric acid, wherein the term "a subject in need" refers to a subject whose TGM1 gene, KRT1 gene, KRT10 gene, KRT14 gene, FLG gene, GBA gene and HAS3 gene are deleted, mutated, or low-expressed, or a subject having poor skin moisturization or dry skin. In the method as described above, the adopted 2-hydroxy-3-methylbutyric acid can be administered to the subject in need in a form of the aforesaid pharmaceutical, food or cosmetic composition and the administration type, administration route, administration form, administration frequency, and uses of the pharmaceutical, food or cosmetic composition are all in line with the above descriptions.

The present invention will be further illustrated in detail with specific examples as follows. However, the following examples are provided only for illustrating the present invention and the scope of the present invention is not limited thereby. The scope of the present invention will be indicated in the appended claims.

EXAMPLE

In the following examples, the materials and equipment are described as below:
1. seawater agar (per liter): NaCl (24.32 g), $MgCl_2.6H_2O$ (5.14 g), $Na_2SO_4$ (4.06 g), KCl (0.69 g), $CaCl_2).2H_2O$ (1.14 g), trace element solution (10 mL), tryptone (1 g), yeast extract (0.5 g), and agar (15 g); pH 7.2, wherein the trace element solution (per liter) contains 0.01 g of $H_2SeO_3$, 0.10 g of $MnCl_2.4H_2O$, 0.10 g of $FeSO_4.7H_2O$, 0.15 g of $CoCl_2.6H_2O$, 0.10 g of $ZnCl_2$, 0.01 g of $H_3BO_3$, 0.01 g of $NaMoO_4.2H_2O$, 0.02 g of $CuCl_2.2H_2O$, 0.02 g of $NiSO_4.6H_2O$, 0.04 g of $AlCl_3.6H_2O$, 0.50 g of disodium EDTA dehydrate and 0.03 g of $Na_2WO_4.6H_2O$.
2. seawater-like medium: using double-distilled water ($ddH_2O$) as a base, wherein the double-distilled water (per liter) contains 2 g of glucose, 10 g of yeast extract, 4.3 g of $MgSO_4.7H_2O$, 25 g of NaCl, 0.9 g of $KH_2PO_4$, and 1.8 g of $K_2HPO_4$.
3. keratinocyte serum-free medium: Keratinocyte-SFM, purchased from Thermo, product no.: 17005042.
4. human epidermal keratinocytes HPEK-50 (purchased from CELLnTEC).
5. column chromatography: macroporous resin, 100 cm×8 cm; purchased from Mitsubishi Chemical Co., Japan, product no.: Diaion HP-20.
6. normal phase silica column chromatography: column: 30 cm×5 cm; silica: purchased from Germany Merck, product no.: Silica gel 60 (0.015-0.040 mm).
7. materials related to thin layer chromatography (TLC): thin layer chromatography silica film 60 $F_{254}$, thin layer chromatography aluminum plate RP-18 $F_{254}$-S; purchased from Germany Merck, EMD Millipore Co.
8. medium pressure liquid chromatography: purchased from Teledyne ISCO, USA, product no.: CombiFlash® Rf+.
9. reversed phase high performance liquid chromatography: Agilent 1200 series deaerator (purchased from Agilent, Germany, G1322A); Agilent 1200 series quaternary pump (purchased from Agilent, Germany, G1311A); Agilent 1260 Infinity 1260 DAD VL (purchased from Agilent, Germany, G1315D); Agilent 1200 series visible light wavelength detector (purchased from Agilent, Germany, G1314B); 250 mm×10 mm column (purchased from Phenomenex, USA, product no.: Luna 5u RP-C18).
10. nuclear magnetic resonance: purchased from Bruker Co., product no.: Ascend 400'54 400 MHz.
11. ultra performance liquid chromatography-mass spectrometry (UPLC-MS/MS): ultra performance liquid chromatography was purchased from Thermo, product no.: Ultimate 3000; mass spectrometry was purchased from Germany Bruker, product no.: BRUKER APEX II mass spectrometer; column (250 mm×4.6 mm) was purchased from Phenomenex, USA, product no.: Luna 5u RP-C18.

Preparation Example

A. Selection and Identification of *Alteromonas macleodii* Dow02-2

A-1. Selection

Inventors of the present invention took a sample from the deep ocean water reservoir of Taiwan Yes Deep Ocean Water Co., Ltd. The sample thus collected was spread onto a seawater agar and then the agar was incubated at 25° C. for 3 days. Thereafter, a single colony was picked up by using a sterilized inoculating loop to perform the following 16S rRNA bacterial identification.

A-2. Identification

A strain of the single colony selected from A-1 was subjected to a phylogenetic analysis, and it was confirmed that the strain has a 16S rRNA fragment with a sequence as shown in SEQ ID NO: 1. SEQ ID NO: 1 was compared to the online database of National Center for Biotechnology Information (NCBI), and it was noted that SEQ ID NO: 1 has an identity of about 98% to the 16S rRNA fragment of *Alteromonas macleodii* strain. Hence, the strain selected from A-1 was identified as an *Alteromonas macleodii* strain according to the phylogenetic relationship and was named as *Alteromonas macleodii* Dow02-2.

A-3. Storage

The unique strain obtained from A-1 was subjected to a liquid culture with a seawater-like medium to provide a bacterial solution. Thereafter, glycerol was added into the bacterial solution to make a final concentration of 25%, and then the mixture thus obtained was placed into collection tubes and stored at a temperature of −80° C.

B. Preparation of metabolites of *Alteromonas macleodii* Dow02-2

The collection tube containing *Alteromonas macleodii* Dow02-2 obtained from A-3 was thawed, and then Dow02-2 strain was inoculated into a seawater-like medium and cultured at 28° C. to activate the strain. Thereafter, the Dow02-2 strain activated once was inoculated into a seawater-like medium at an inoculum concentration of 1% (about $10^5$ CFU/mL) and cultured at 28° C. for 18 hours to provide a bacterial solution of *Alteromonas macleodii* Dow02-2. Then, the bacterial solution was subjected to a centrifugation, and the supernatant thus obtained was collected for use in the following experiments.

C. Isolation and Identification of 2-Hydroxy-3-Methylbutyric Acid

C-1.

10 L of the supernatant obtained from [Preparation Example] B was concentrated under vacuum until its volume was decreased to 2 L. Thereafter, the concentrated metabolites was subjected to a column chromatography (mobile phase gradient: from pure water to methanol), so as to obtain fraction 1 (pure water elute; totally 158.9 g), fraction 2 (20% methanol elute; totally 18.3 g), fraction 3 (40% methanol elute; totally 13.4 g), fraction 4 (60% methanol elute; totally 9.7 g), and fraction 5 (100% methanol elute; totally 7.3 g).

C-2.

The fraction 5 obtained from C-1 was subjected to a normal phase silica column chromatography (mobile phase: the mobile phase I to XIII as listed in Table 1) to obtain 90 elutes (as shown in Table 1). And then, the 90 elutes were analyzed by a thin layer chromatography, and based on the analysis results, the similar elutes were combined. Finally, 16 subfractions were obtained (as shown in Table 2).

TABLE 1

| Mobile phase | Component(s) and volume ratio | Elute(s) |
| --- | --- | --- |
| I | 100% n-hexane | 1 to 4 |
| II | n-hexane:ethyl acetate = 9:1 | 5 to 8 |
| III | n-hexane:ethyl acetate = 4:1 | 9 to 14 |
| IV | n-hexane:ethyl acetate = 7:3 | 15 to 22 |
| V | n-hexane:ethyl acetate = 1:1 | 23 to 32 |
| VI | n-hexane:ethyl acetate = 3:7 | 33 to 40 |
| VII | 100% ethyl acetate | 41 to 50 |
| VIII | ethyl acetate:methanol = 9:1 | 51 to 58 |
| IX | ethyl acetate:methanol = 4:1 | 59 to 66 |
| X | ethyl acetate:methanol = 7:3 | 67 to 72 |
| XI | ethyl acetate:methanol = 1:1 | 73 to 78 |
| XII | ethyl acetate:methanol = 3:7 | 79 to 84 |
| XIII | 100% methanol | 84 to 90 |

TABLE 2

| Subfraction | Elute(s) | Subfraction | Elute(s) |
| --- | --- | --- | --- |
| 1 | 1 to 4 | 9 | 45 to 51 |
| 2 | 5 to 8 | 10 | 52 to 57 |
| 3 | 9 to 15 | 11 | 58 to 64 |
| 4 | 16 to 21 | 12 | 65 to 69 |
| 5 | 22 to 24 | 13 | 70 to 74 |
| 6 | 25 to 33 | 14 | 75 to 81 |
| 7 | 34 to 38 | 15 | 82 to 84 |
| 8 | 39 to 44 | 16 | 85 to 90 |

C-3.

The subfraction 11 obtained from C-2 (totally 1,218 mg) was subjected to a medium pressure liquid chromatography (MPLC; mobile phase gradient: a linear gradient from pure water to 50% methanol; detection wavelength: 210 nm) for 30 minutes. 5 sub-subfractions were thus obtained.

C-4.

The first sub-subfraction obtained from C-3 was subjected to a reversed phase high performance liquid chromatography (RP-HPLC; mobile phase: 10% aqueous methanol solution; detection wavelength: 210 nm; flow speed: 30 mL/min). A compound (totally 4.3 mg) was thus obtained and named as TCI-OceanO2-01.

C-5.

Figure 1:
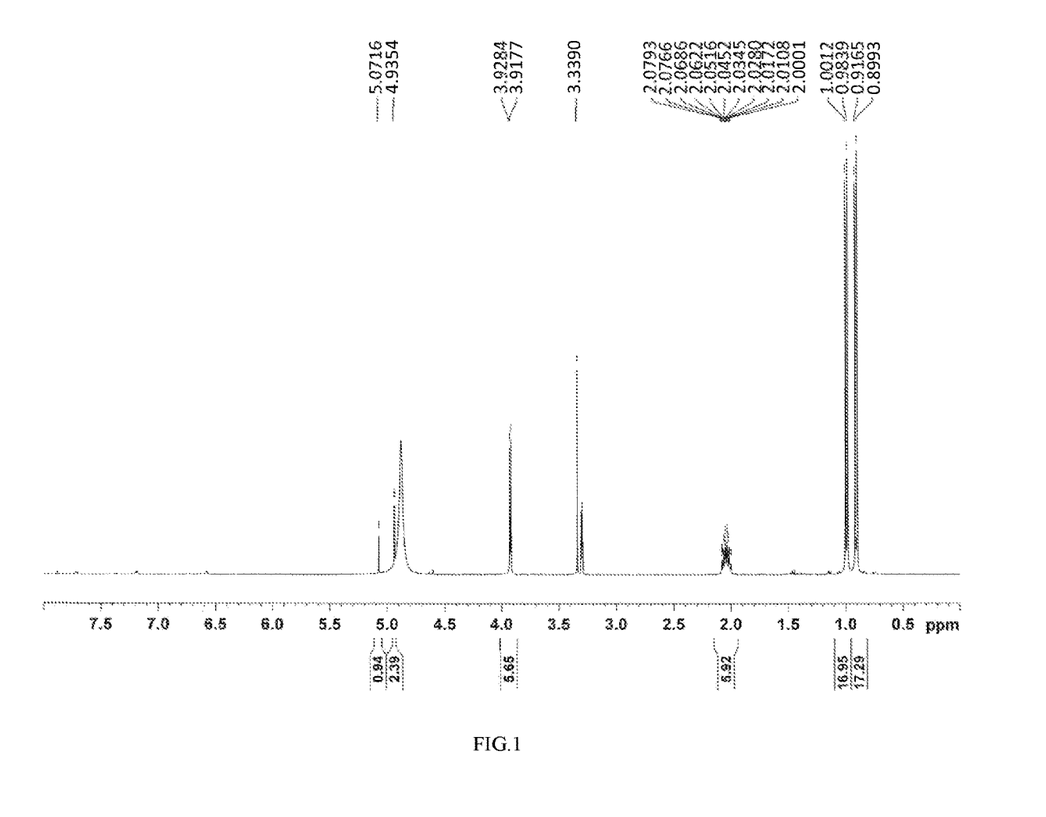
FIG. 1 is a $^1$H nuclear magnetic resonance spectrum of TCI-OceanO2-01 compound, which was isolated from the metabolites of *Alteromonas macleodii* Dow02-2.
Figure 2:
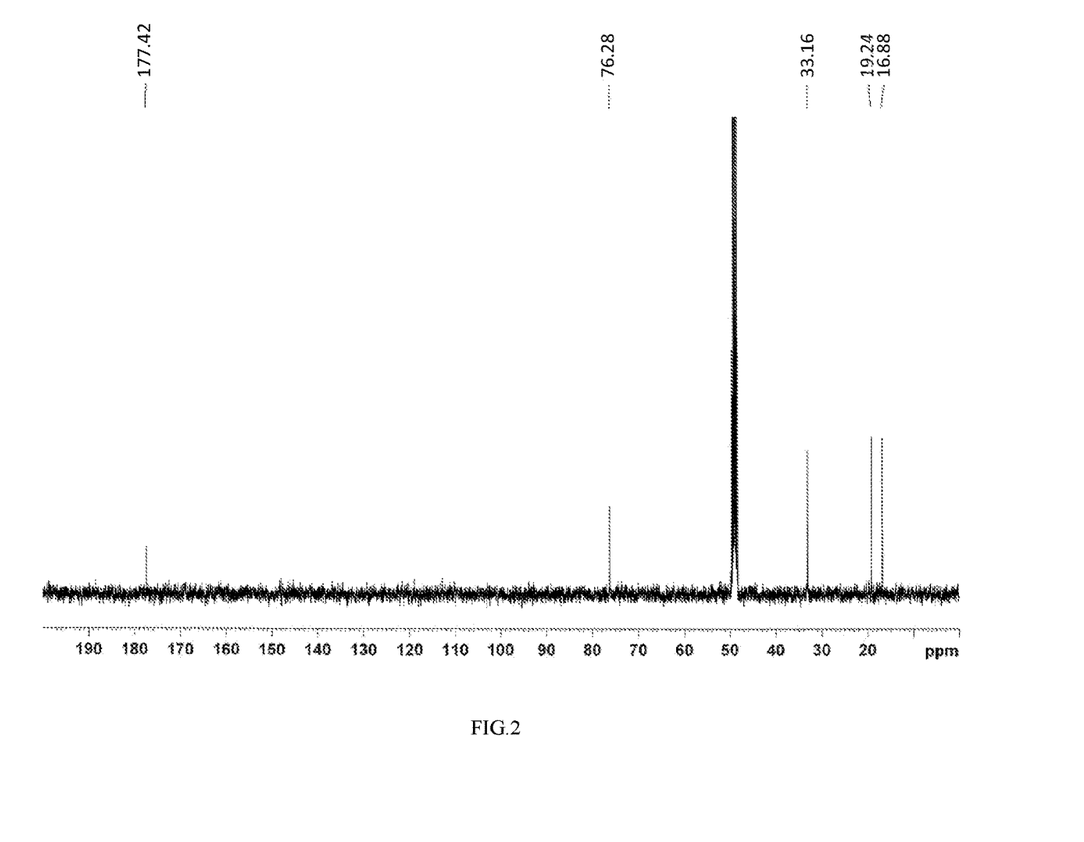
FIG. 2 is a $^{13}$C nuclear magnetic resonance spectrum of TCI-OceanO2-01 compound, which was isolated from the metabolites of *Alteromonas macleodii* Dow02-2.
Figure 3:
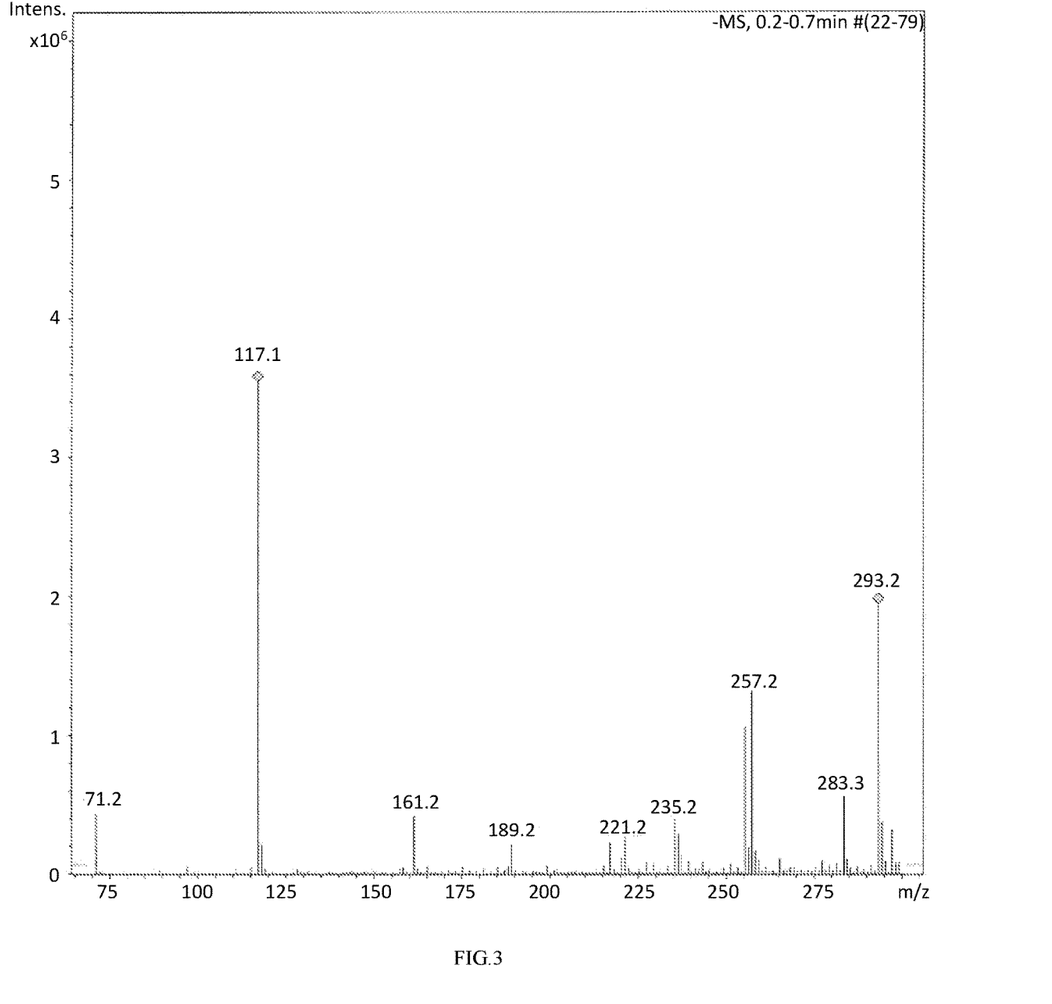
FIG. 3 is an electrospray ionization mass spectrometry (negative ion mode) spectrum of TCI-OceanO2-01 compound, which was isolated from the metabolites of *Alteromonas macleodii* Dow02-2.

On one hand, the TCI-OceanO2-01 compound obtained from C-4 was analyzed by a $^1$H-nuclear magnetic resonance (NMR), $^{13}$C-nuclear magnetic resonance, and electrospray ionization mass spectrometry (ESIMS), wherein the condition of $^1$H-NMR (400 MHz in MeOH-$d_4$) was 3.92 (d, J=4.3 Hz, 1H), 2.05 (m, 1H), 0.99 (d, J=6.9 Hz, 3H), and 0.91 (d, J=6.9 Hz, 3H); the condition of $^{13}$C-NMR (100 MHz in MeOH-$d_4$) was 177.42, 76.28, 33.16, 19.24, 16.88; the condition of ESI-MS was 117 (M-H)$^-$. The results are shown in FIGS. 1 to 3. Through analyzing the results of FIGS. 1 to 3, the TCI-OceanO2-01 compound should be 2-hydroxy-3-methylbutyric acid (also called 2-hydroxy-3-methyl-butanoic acid).

Figure 4:
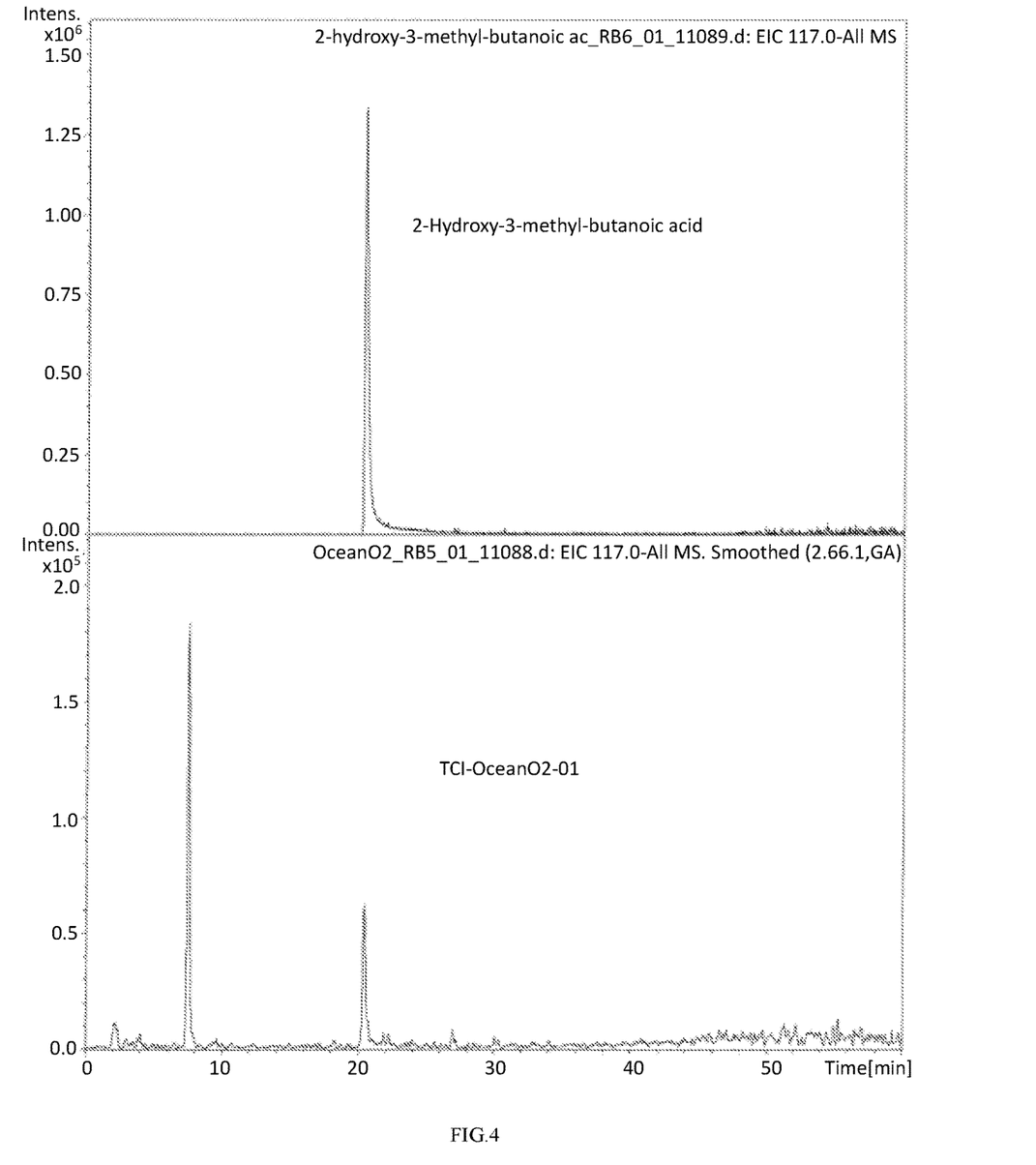
FIG. 4 is an ultra performance liquid chromatography-mass spectrometry (UPLC-MS/MS) spectrum of the metabolites of *Alteromonas macleodii* Dow02-2 and standard of 2-hydroxy-3-methylbutyric acid (top portion: the result of the standard of 2-hydroxy-3-methylbutyric acid; bottom portion: the result of the first sub-subfraction obtained from C-3).
Figure 5:
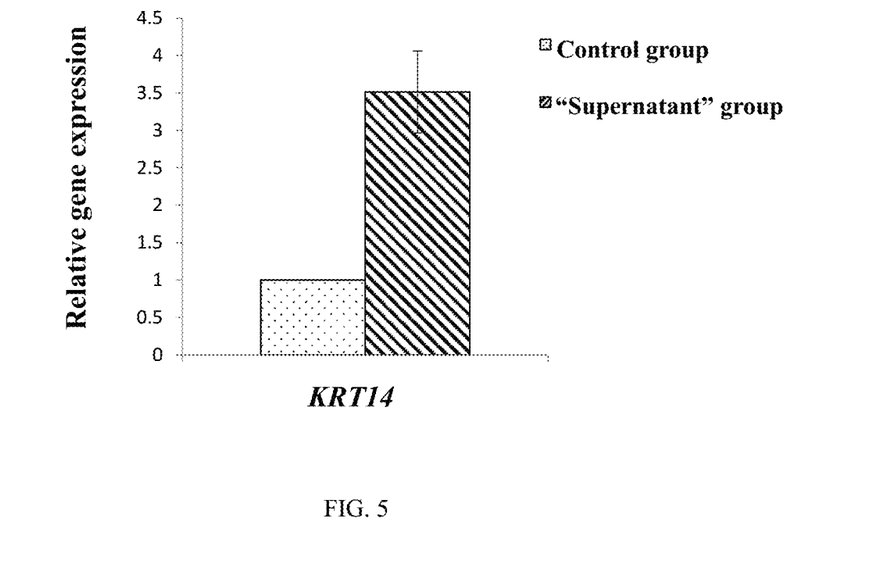
FIG. 5 shows that in comparison with the control group, the relative expression level of KRT14 gene in human epidermal keratinocytes HPEK-50 of the "Supernatant" group, wherein the cells in the control group were cultured with a keratinocyte serum-free medium (keratinocyte-SFM), and those in the "Supernatant" group were cultured with a keratinocyte-SFM that was additionally added with 62.5 μm/ml of the supernatant obtained from [Preparation Example] B.
Figure 6:
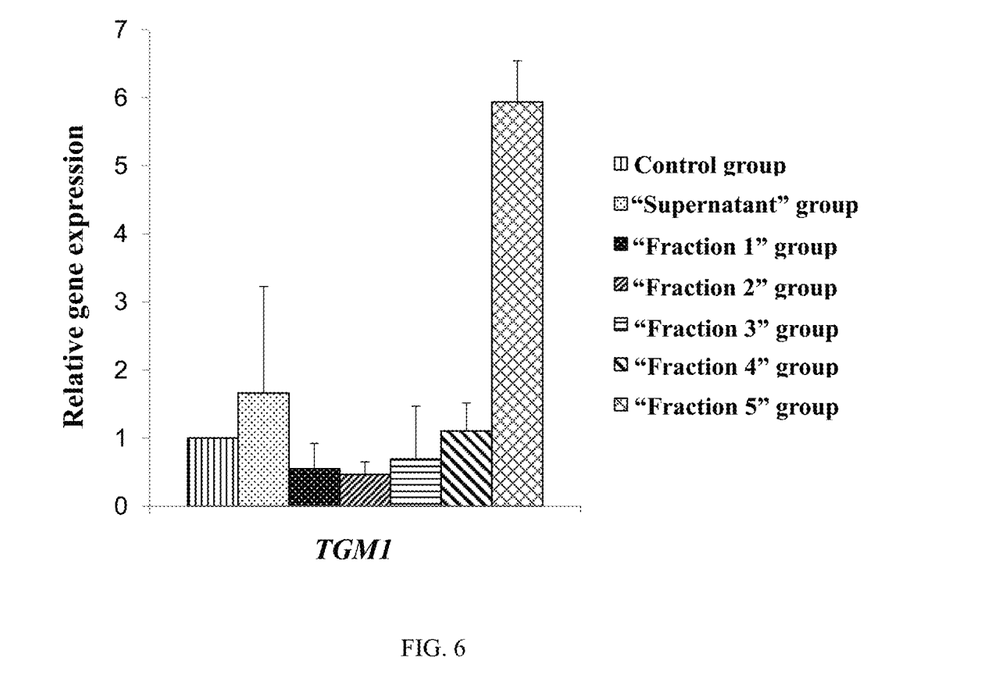
FIGS. 6 to 8 respectively show that in comparison with the control group, the relative expression levels of TGM1, FLG and HAS3 genes in human epidermal keratinocytes HPEK-50 of each group. The cells in the control group were cultured with a keratinocyte-SFM. Those in the "Supernatant" group were cultured with a keratinocyte-SFM that was additionally added with 62.5 μg/ml of the supernatant obtained from [Preparation Example] B. Those in "Fraction 1" to "Fraction 5" were respectively cultured with a keratinocyte-SFM that was additionally added with 62.5 μg/ml of the fraction 1, 2, 3, 4 or 5 obtained from [Preparation Example] C-1.
Figure 7:
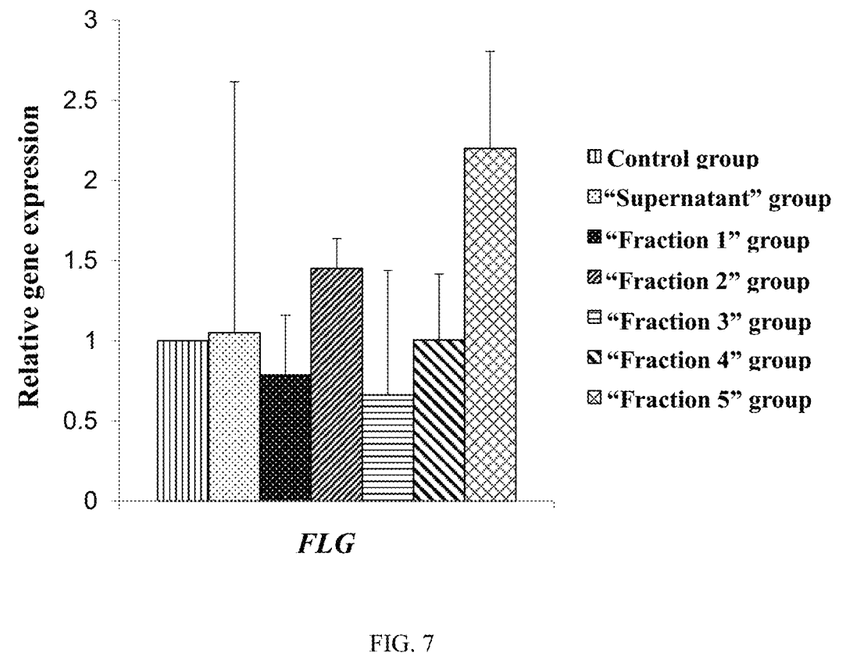
Figure 8:
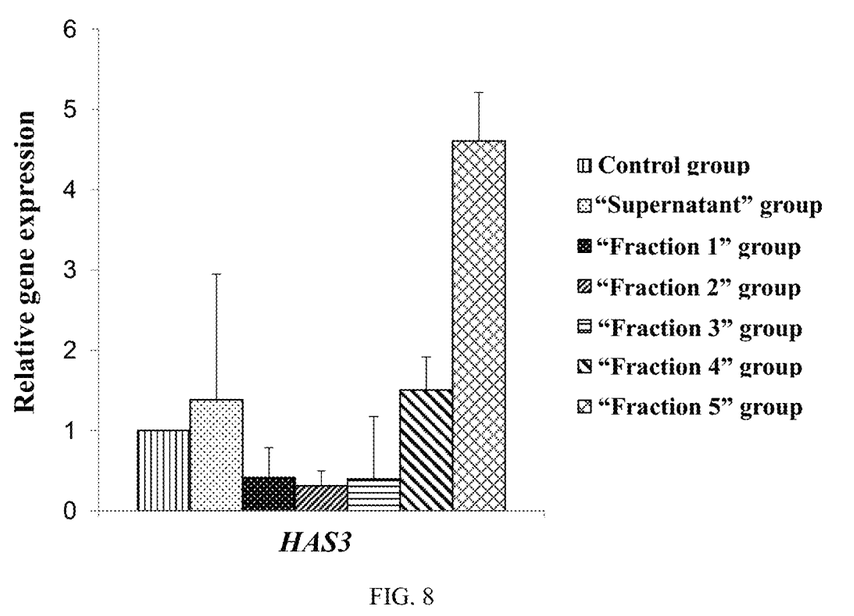
Figure 9:
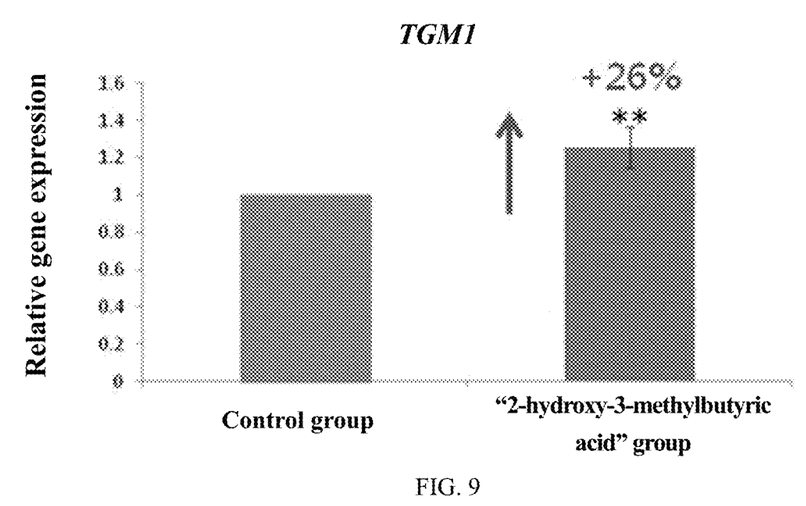
FIGS. 9 to 15 respectively show that in comparison with the control group, the relative expression levels of TGM1, KRT1, KRT10, KRT14, FLG, GBA and HAS3 genes in human epidermal keratinocytes HPEK-50 of the "2-hydroxy-3-methylbutyric acid" group (* indicates that the result has a significant difference to that of the control group with a p value<0.05; ** indicates that the result has a significant difference to that of the control group with a p value<0.01). The cells in the control group were cultured with a keratinocyte-SFM, and those in the "2-hydroxy-3-methylbutyric acid" group were cultured with a keratinocyte-SFM that was additionally added with 10 μg/ml of TCI-OceanO2-01 compound (i.e., 2-hydroxy-3-methylbutyric acid) obtained from [Preparation Example] C-4.
Figure 10:
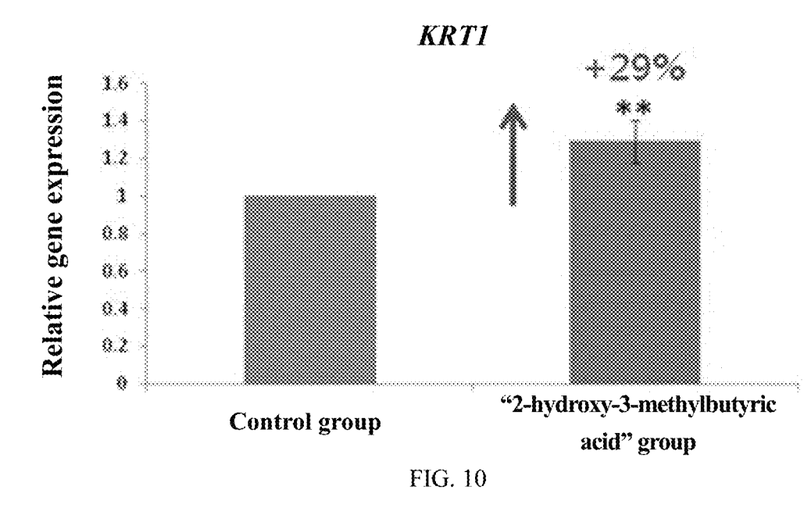
Figure 11:
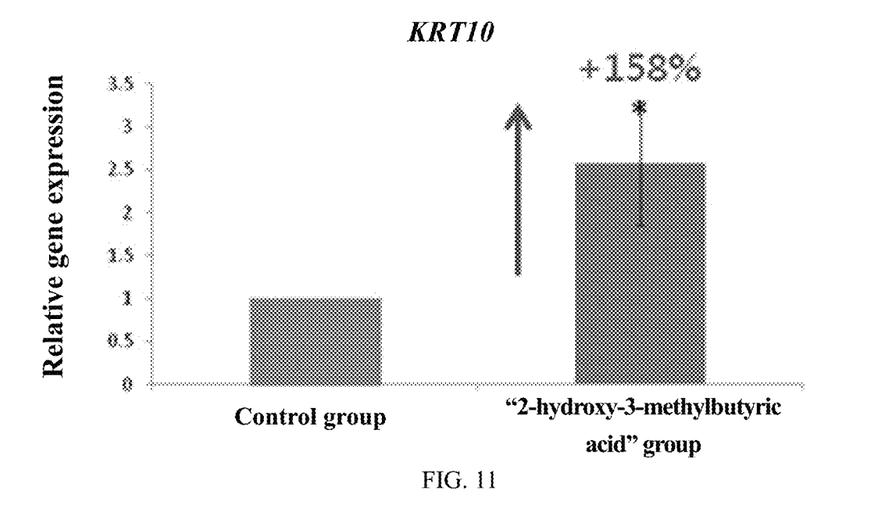
Figure 12:
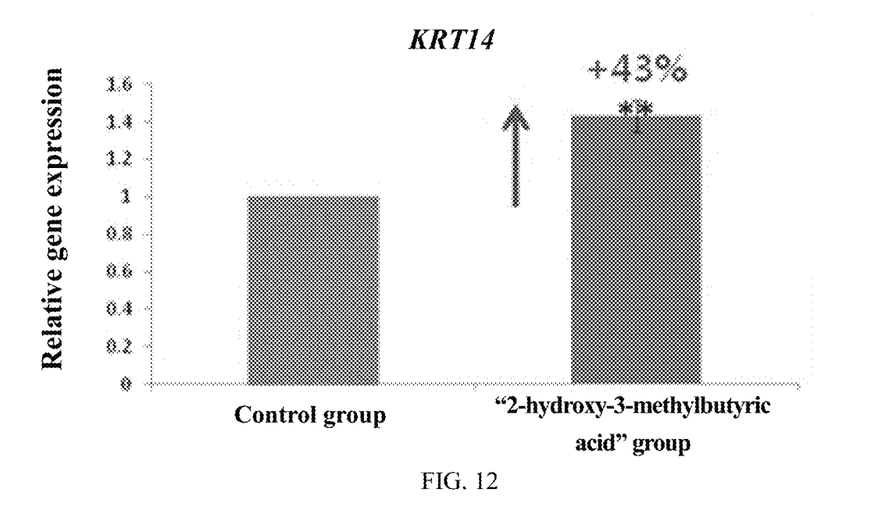
Figure 13:
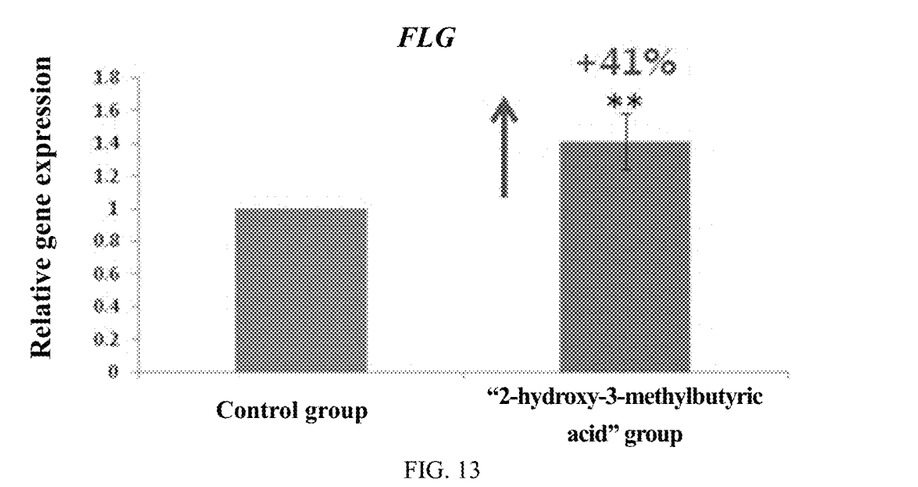
Figure 14:
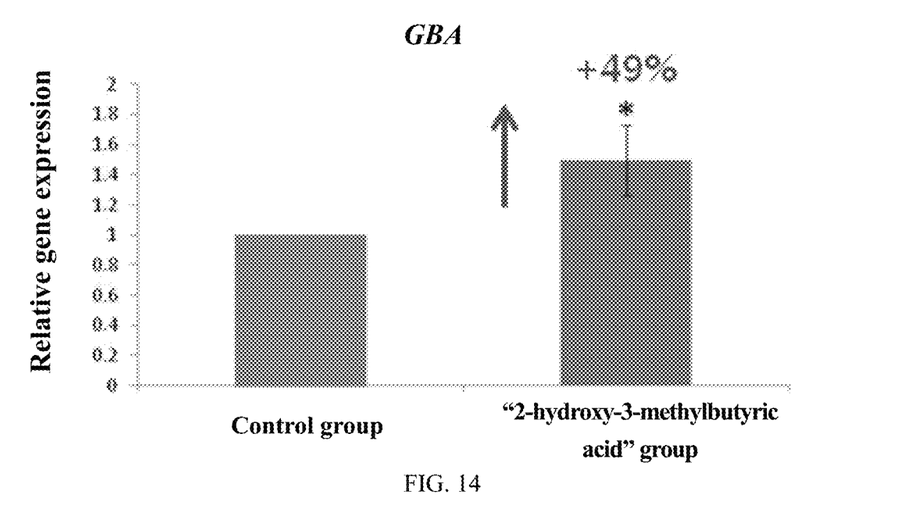
Figure 15:
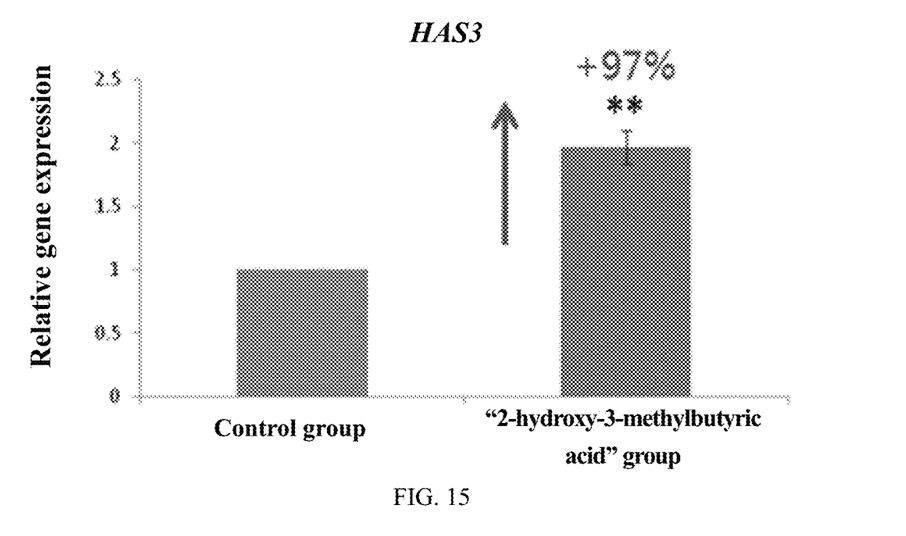

On the other hand, a standard of 2-hydroxy-3-methylbutyric acid (purchased from Sigma-Aldrich, purity>98%) and the supernatant obtained from [Preparation Example] B were analyzed by an ultra performance liquid chromatography-mass spectrometry (mobile phase was as shown in the following Table 3; flow speed: 1 mL/min). The results are shown in FIG. 4 (top portion: the result of the standard of 2-hydroxy-3-methylbutyric acid; bottom portion: the result of the first sub-subfraction obtained from C-3). As shown in FIG. 4, the peak of the TCI-OceanO2-01 compound can correspond to that of the standard of 2-hydroxy-3-methyl-butyric acid. The aforesaid results show that the TCI-OceanO2-01 compound is 2-hydroxy-3-methylbutyric acid. In addition, through calculating the yield of the TCI-OceanO2-01 compound isolated by ultra performance liquid chromatography, the concentration of TCI-OceanO2-01 compound in the supernatant obtained from [Preparation Example] B is about 2.5 ppm.

TABLE 3

| Analysis time (minute) | Mobile phase |
| --- | --- |
| 0 | methanol:water = 1:45 |
| 10 | methanol:water = 1:45 |
| 40 | methanol:water = 7:3 |
| 50 | 100% methanol |
| 60 | 100% methanol |

Example 1: Effects of Metabolites of *Alteromonas macleodii* Dow02-2 and 2-Hydroxy-3-Methylbutyric Acid on Moisturizing Skin 1-1. Cells Treatment The human epidermal keratinocytes HPEK-50 were cultured with a keratinocyte-SFM at 37° C. for 24 hours. Thereafter, the cells were divided into eight groups and respectively cultured with the following media at 37° C. for 6 hours:

1. Control group: keratinocyte-SFM;
2. "Supernatant" group: keratinocyte-SFM that was additionally added with 62.5 μg/ml of the supernatant obtained from [Preparation Example] B;

3. "Fraction 1" group: keratinocyte-SFM that was additionally added with 62.5 μg/ml of the Fraction 1 obtained from [Preparation Example] C-1;
4. "Fraction 2" group: keratinocyte-SFM that was additionally added with 62.5 μg/ml of the Fraction 2 obtained from [Preparation Example] C-1;
5. "Fraction 3" group: keratinocyte-SFM that was additionally added with 62.5 μg/ml of the Fraction 3 obtained from [Preparation Example] C-1;
6. "Fraction 4" group: keratinocyte-SFM that was additionally added with 62.5 μg/ml of the Fraction 4 obtained from [Preparation Example] C-1;
7. "Fraction 5" group: keratinocyte-SFM that was additionally added with 62.5 μg/ml of the Fraction 5 obtained from [Preparation Example] C-1; and
8. "2-hydroxy-3-methylbutyric acid" group: keratinocyte-SFM that was additionally added with 10 μg/ml of the TCI-OceanO2-01 compound obtained from [Preparation Example] C-4 (i.e., 2-hydroxy-3-methylbutyric acid).

1-2. Moisturizing-Related Gene Expression

To investigate the effects of metabolites of *Alteromonas macleodii* Dow02-2 and 2-hydroxy-3-methylbutyric acid on moisturizing skin, inventors of the present invention collected the cells in each group of Example 1-1. The cells were subjected to an RNA extraction with an RNA purification kit (purchased from Geneaid). Then, the RNA was retro-transcribed into cDNA by using a SuperScript™ III Reverse Transcriptase kit (purchased from Invitrogen). Thereafter, the cDNA was subjected to a quantitative polymerase chain reaction (qPCR) by using a KAPA CYBR FAST qPCR kit (purchased from KAPA Biosystems) and ABI StepOne Plus™ System to determine the expression levels of moisturizing-related genes such as TGM1 gene, KRT1 gene, KRT10 gene, KRT14 gene, FLG gene, GBA gene and HAS3 gene in the cells of each group. Then, the relative gene expression of each group was calculated by using the result of the control group as a basis (i.e., set the gene expression of the control group as 1-fold). The results are shown in FIG. 5 to FIG. 15.

As shown in FIGS. 5 to 8, in comparison with the control group, the expression levels of KRT14 gene, TGM1 gene, FLG gene, and HAS3 gene in the cells of the "Supernatant" group and "Fraction 5" group were significantly increased. That is, the metabolites of *Alteromonas macleodii* Dow02-2 are indeed effective in increasing expressions of moisturizing-related genes such as KRT14, TGM1, FLG and HAS3 genes, and thus can be used for improving skin moisturization.

As shown in FIGS. 9 to 15, in comparison with the control group, the expression levels of TGM1 gene, KRT1 gene, KRT10 gene, KRT14 gene, FLG gene, GBA gene and HAS3 gene in the cells of the "2-hydroxy-3-methylbutyric acid" group were respectively increased 26%, 29%, 158%, 43%, 41%, 49% and 97%. That is, the 2-hydroxy-3-methylbutyric acid can also be used for improving skin moisturization.

The above results show that, the metabolites of *Alteromonas macleodii* Dow02-2 of the present invention comprise 2-hydroxy-3-methylbutyric acid, and the metabolites of *Alteromonas macleodii* Dow02-2 and 2-hydroxy-3-methylbutyric acid are both effective in increasing expressions of TGM1, KRT1, KRT10, KRT14, FLG, GBA and HAS3 genes. Therefore, *Alteromonas macleodii* Dow02-2 of the present invention can be used for providing 2-hydroxy-3-methylbutyric acid, and the metabolites of *Alteromonas macleodii* Dow02-2 and 2-hydroxy-3-methylbutyric acid both can be used for improving skin moisturization.

Deposit of Biological Material

Depository institute: German Collection of Microorganisms and Cell Cultures (Deutsche Sammlung von Mikroorganismen and Zellkulturen, DSMZ)

Address: Inhoffenstraße 7 B, 38124 Braunschweig, GERMANY
Date: 2019 Nov. 25
Deposited biological material: *Alteromonas macleodii* Dow02-2
Accession number: DSM33380

What is claimed is:

1. A method for increasing expression of at least one of TGM1 gene, KRT1 gene, KRT10 gene, KRT14 gene, FLG gene, GBA gene, and HAS3 gene in human epidermal keratinocytes, wherein the method comprises administering to a subject in need an effective amount of 2-hydroxy-3-methylbutyric acid.

2. The method as claimed in claim 1, wherein the 2-hydroxy-3-methylbutyric acid is administered to the subject in a form of a food composition or a cosmetic composition.

3. The method as claimed in claim 1, wherein the 2-hydroxy-3-methylbutyric acid is used in a form of metabolites of an *Alteromonas macleodii* Dow02-2, and the *Alteromonas macleodii* Dow02-2 was deposited at German Collection of Microorganisms and Cell Cultures (Deutsche Sammlung von Mikroorganismen and Zellkulturen, DSMZ) under the accession number DSM33380.

4. The method as claimed in claim 1, wherein the method is for improving skin moisturization.

5. The method as claimed in claim 4, wherein the 2-hydroxy-3-methylbutyric acid is administered to the subject in a form of a food composition or a cosmetic composition.

6. The method as claimed in claim 4, wherein the 2-hydroxy-3-methylbutyric acid is used in a form of metabolites of an *Alteromonas macleodii* Dow02-2, and the *Alteromonas macleodii* Dow02-2 was deposited at German Collection of Microorganisms and Cell Cultures (Deutsche Sammlung von Mikroorganismen and Zellkulturen, DSMZ) under the accession number DSM33380.

* * * * *